United States Patent [19]
Devonec et al.

[11] Patent Number: 5,876,417
[45] Date of Patent: Mar. 2, 1999

[54] DETACHABLE CATHETER APPARATUS

[76] Inventors: Marian Devonec, 81 avenue des Balmes, 01700 Miribel, France; Les Sherwood, 5008 Harvest Ct., Bloomington, Ind. 47404; Joe Desmond, 3123 Ryan Ct., Bloomington, Ind. 47403

[21] Appl. No.: 679,393

[22] Filed: Jul. 9, 1996

[30] Foreign Application Priority Data

Jul. 10, 1995 [FR] France .................................. 95 08682

[51] Int. Cl.⁶ .................................................. A61M 29/00
[52] U.S. Cl. ......................................................... 606/192
[58] Field of Search ........................... 606/192; 604/164, 604/96, 104, 101

[56] References Cited

U.S. PATENT DOCUMENTS

| | | | |
|---|---|---|---|
| 3,833,003 | 9/1974 | Taricco | 606/192 X |
| 3,837,347 | 9/1974 | Tower | 606/192 X |
| 4,423,725 | 1/1984 | Baran et al. | |
| 4,465,072 | 8/1984 | Taheri | 606/192 X |
| 5,078,720 | 1/1992 | Burton et al. | |
| 5,135,535 | 8/1992 | Kramer | 606/192 X |
| 5,445,645 | 8/1995 | Debbas | 606/192 |
| 5,458,612 | 10/1995 | Chin | 606/192 |

FOREIGN PATENT DOCUMENTS

| | | |
|---|---|---|
| 0 341 988 B1 | 11/1989 | European Pat. Off. . |
| WO 94/18907 | 9/1994 | WIPO . |

OTHER PUBLICATIONS

R. Robert De Nicola, "Permanent Artificial (Silicone) Urethra," The Journal of Urology, vol. 63, No. 1, Jan. 1950, pp. 168–172.

L.A. Loizou, M.D., et al., "Treatment of malignant strictures of the cervical esophagus by endoscopic intubation using modified endoprostheses," Gastrointestinal Endoscopy, 1992, pp. 158–164.

*Primary Examiner*—Manuel Mendez
*Attorney, Agent, or Firm*—Oliff & Berridge, PLC

[57] ABSTRACT

A detachable catheter apparatus that conveys a fluid includes a tube assembly and an insertion device. The tube assembly extends along a longitudinal axis and includes a distal tube section having a closed end and an opposite opened end, a proximal tube section having a first end and an opposite second end and a connector fabricated from a flexible, deformable material. The connector connects the opened end of the distal tube section and the first end of the proximal tube section together. The distal tube section includes an orifice formed therethrough and sized to enable fluid to enter the distal tube section so that the fluid can flow into and through the distal tube section, the connector and the proximal tube section. The insertion device is slidably receivable by the tube assembly, and includes an elongated inner alignment rod having a contact end portion and an insertion end portion disposed opposite the contact end portion. The inner alignment rod is sized to extend into the tube assembly so that the contact end portion contacts the closed end of the distal tube section while the insertion end portion projects outwardly from the tube assembly.

14 Claims, 4 Drawing Sheets

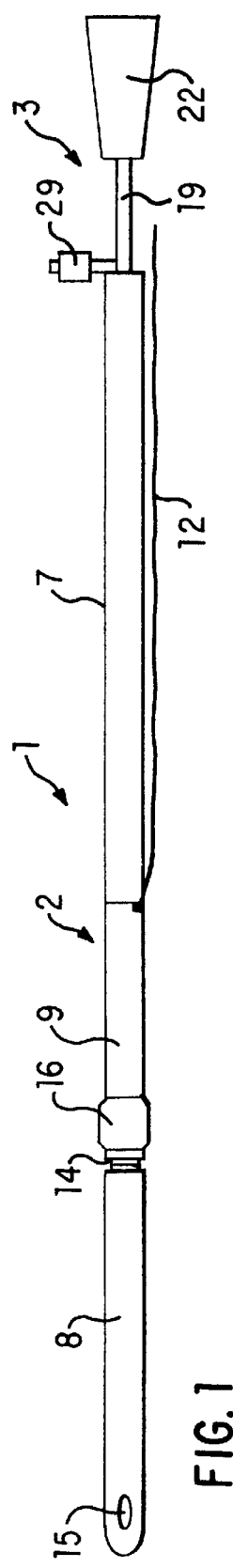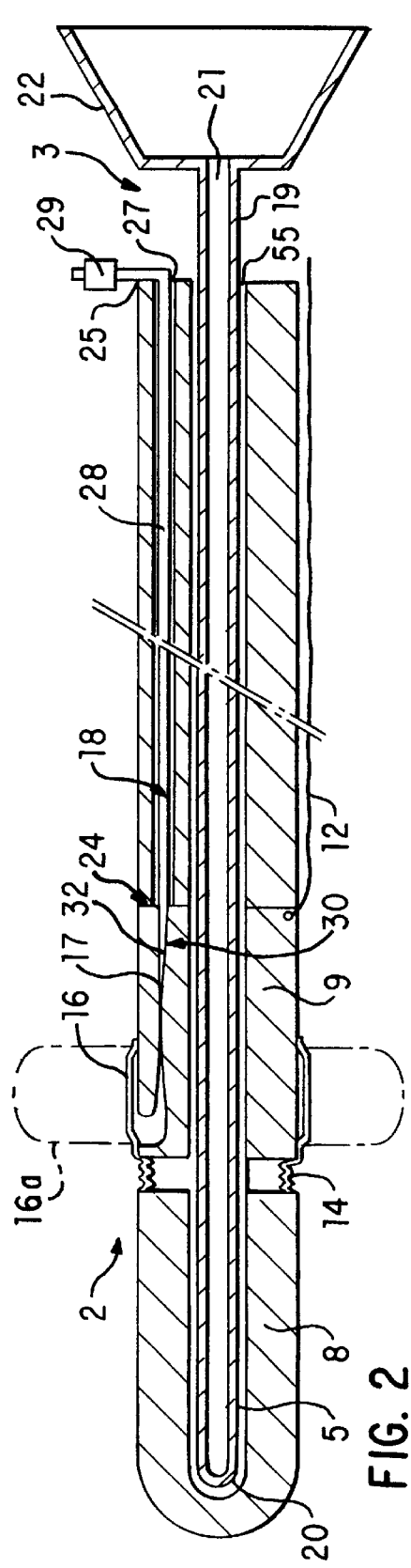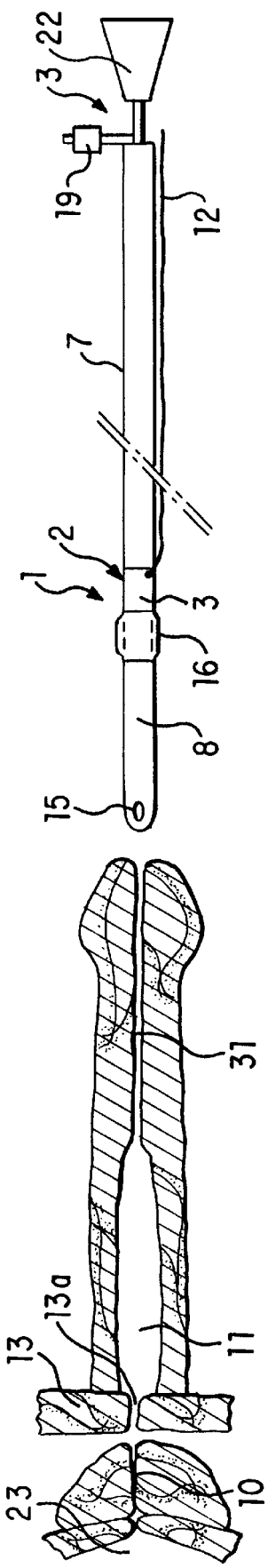

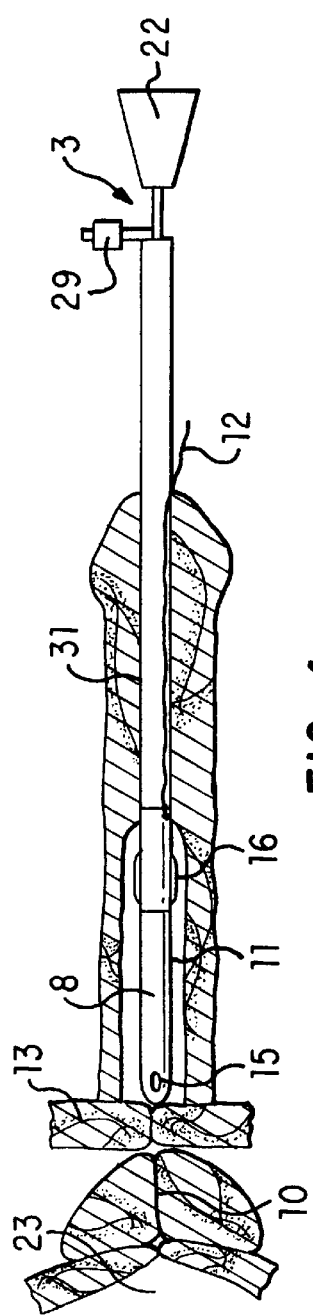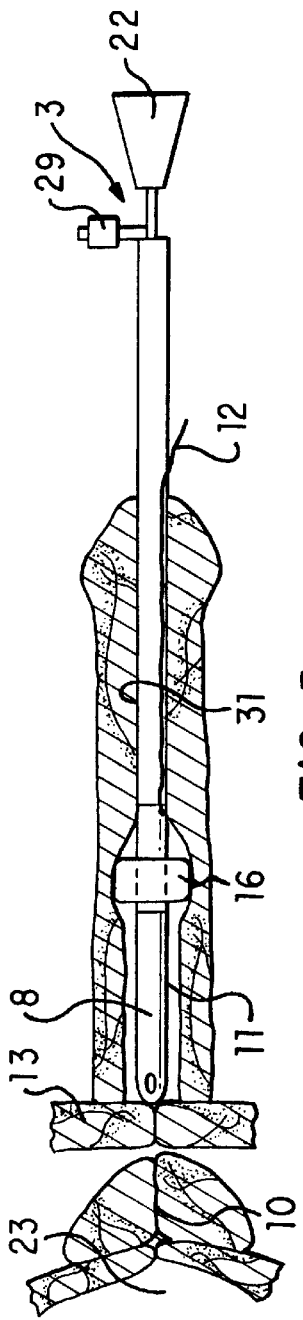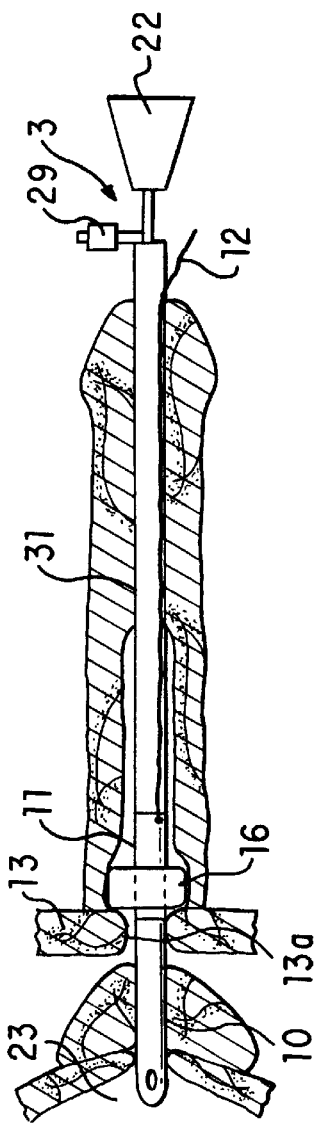

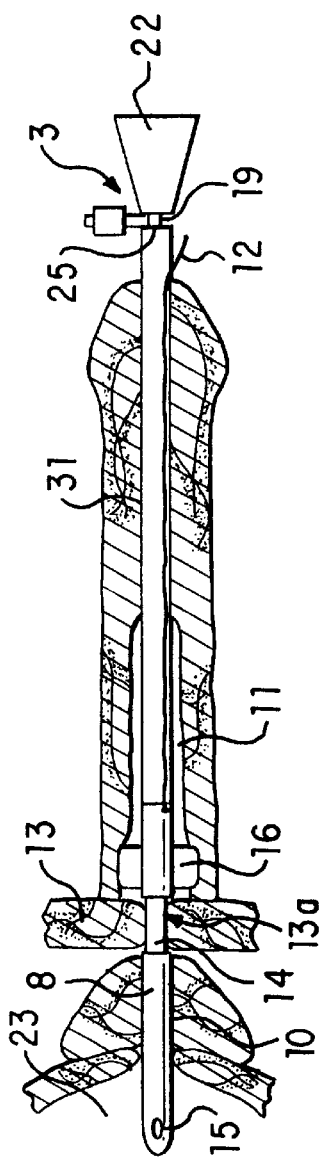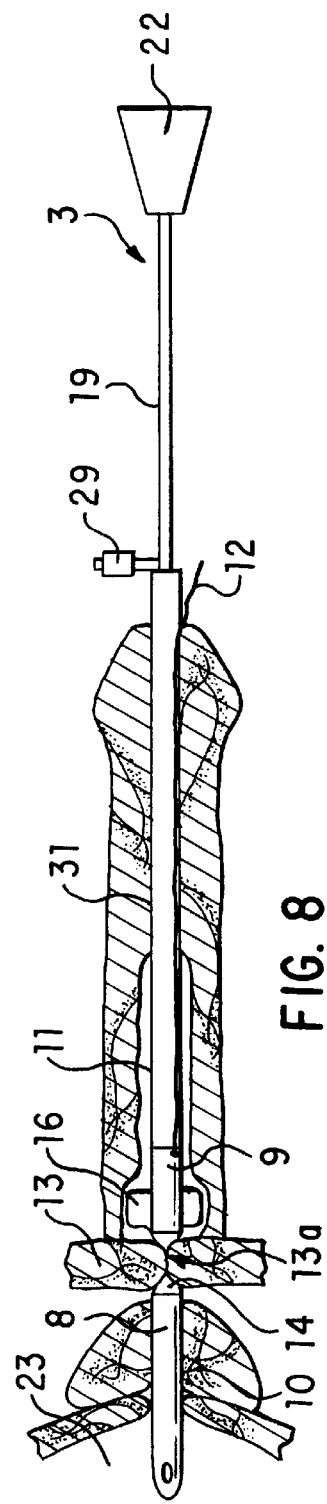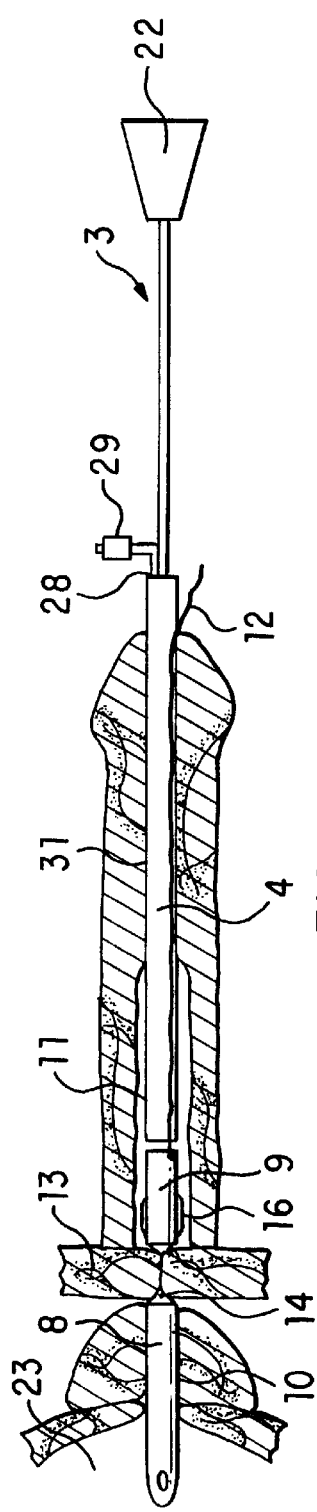

DETACHABLE CATHETER APPARATUS

The present invention relates to a separable catheter which is intended to be used in the treatment of prostate obstructions in humans.

The technical solutions proposed for treating prostate obstructions are well known in the prior art. These solutions generally involve the positioning of an intraurethral catheter (IUC) in which a free passage is created between the bladder and the outside of the human body in such a way as to ensure the permanent outward flow of urine. Such a catheter is the urethral catheter called the Foley catheter or indwelling catheter.

This catheter consists of a tube in one piece (monobloc) which comprises a main lumen for draining the urine and a lumen of small diameter in the wall of the tube, this latter lumen making it possible to inflate a balloon situated in proximity to the distal end of the tube.

The distal end is flexible and includes an orifice which communicates with the main lumen, thereby ensuring the permanent drainage of urine from the bladder, and a balloon situated slightly back from or below the orifice for drainage of urine. Once inflated, the balloon serves to maintain the drainage orifice permanently inside the bladder and to hold the catheter in the urethral channel.

The proximal end of the catheter includes an opening for the drainage of the urine, which opening is in continuity of flow with the main lumen of the tube, and presents a conical shape permitting its connection to a urine collector, as well as an injection/suction valve in continuity with the lumen of small diameter in the wall, which allows the balloon to be inflated and deflated.

This type of catheter ensures a permanent flow of the urine inside the catheter. It is flexible in order to adapt to the different curvatures and angles of the urethra. However, its wall is sufficiently rigid to prevent any crushing or folding of the catheter, which could in particular obstruct the main lumen and impede the flow of urine. The advantages of this system are its straightforward positioning and removal, neither of which require anesthesia.

However, such a catheter has numerous disadvantages, since it is uncomfortable and responsible for complications. This discomfort is due especially to:

the intubation of the urethra along its entire length (from the neck of the bladder to the urethral meatus) using a foreign body, whereas the obstruction is limited to the prostatic segment;

the connection of the catheter to a urine collection system which has to be emptied several times a day;

the permanent flow of urethral secretions along the catheter, necessitating local hygiene measures several times a day;

the impossibility of sexual activity;

and the possible leakage of urine.

Among the complications associated with the use of such catheters, the most common ones are:

urinary tract infection, for example cystitis;

urethral stenosis, more especially in the region of the penoscrotal junction, the region behind the meatus, or the urethral meatus;

the incrustation of the balloon with the salts present in the urine, this incrustation potentially promoting urinary tract infection and the formation of calculi, and hampering the deflation and the removal of the balloon, which then becomes traumatic for the patient; it is consequently necessary to change the catheter every six weeks.

The successful use of such a system depends both on the sensitive and correct manipulation by the physician and on the individual anatomy of each patient.

The present invention thus proposes an improved catheter which remedies the disadvantages associated with the known system described hereinabove.

More particularly, the present invention relates to a catheter which can be positioned in the urethra without the aid of a particular imaging means and which remains relatively independent of the anatomy of the patient to be treated and of the skill of the physician.

In accordance with the invention, the urethral catheter is separable and comprises a distal means of catheterization and a means of introduction which are joined to one another in an aligned manner, for introduction of the catheter into the urethra, and which can be disconnected from one another, for leaving the catheterization means in place in the urethra. This catheter presents the following characteristics in combination:

the catheterization means is relatively flexible so as to adapt in shape to the urethra in the prostatic region, but is sufficiently rigid to maintain an artificial passage in the latter, and it comprises two tubular elements, termed upper and lower respectively, which are intended to be placed in the upper part and lower part, respectively, of the urethral channel, on either side of the striated muscular sphincter, the said tubular elements being connected to one another by a flexible and deformable connection means which lodges itself in the orifice of the striated muscular sphincter;

the introduction means comprises an outer pusher tube, and an inner rod whose external cross section is adapted to the internal cross section of the outer tube, the said introduction means having a length which is adapted in order to intubate the catheterization means as far as the distal end of the upper element;

and, in combination, on the one hand, the catheterization means or the introduction means comprises a distal means for temporary positioning in relation to the lower side of the striated muscular sphincter, and, on the other hand, the introduction means comprises an outer means, for activation of the temporary positioning means, arranged at a proximal end of the introduction means.

The expression "temporary" is to be understood as meaning that the positioning means does not have the function of maintaining the catheterization means in place permanently during the treatment, that is to say in a passive manner, but rather that it can be activated, only upon introduction of the catheter, in order to afford positive assistance to the physician, after which it can be deactivated in order to leave the catheterization means in the correct position in relation to the striated muscular sphincter.

The separable catheter according to the present invention is positioned, by the cooperation of the means defined hereinabove, in relation to the striated muscular sphincter, and not in relation to the neck of the bladder, which fact also allows it to be positioned in a reproducible manner, solely through the awareness of the physician, and without the need for recourse to any instrumental aid for visualization or detection of position.

Furthermore, by providing an upper tubular element of the catheterization means which is sufficiently long in relation to the striated muscular sphincter, it becomes possible to establish a communication with the bladder, irrespective of the size and/or shape of the prostatic part of the urethra, and consequently to provide a single size of catheter.

In one variant of the invention, the temporary positioning means consists of an inflatable balloon, circumscribing the lower tubular element for example, and, in the assembled state of the catheter, communication means connect, on the one hand, the balloon, and, on the other hand, the external activation means, namely an external source of fluid.

In another variant of the invention, the temporary positioning means comprises a plurality of bearing elements distributed about the outer pusher tube and each designed to assume two positions, namely a radially retracted position, and a deployed position protruding radially from the outer pusher tube. And the external activation means is a mechanical means for acting on the bearing elements from a distance, and for making them move from the deployed position to the retracted position, and vice versa.

The present invention will now be described in greater detail with reference to the attached drawing which represents a preferred embodiment, and in which:

FIG. 1 represents a diagrammatic elevation of a separable catheter according to a first embodiment of the invention;

FIG. 2 represents a longitudinal cross sectional view, on an enlarged scale, of the separable catheter in FIG. 1;

FIG. 3 represents diagrammatically a longitudinal cross sectional view of the male prostate region and the catheter in FIG. 1 prior to its introduction;

FIG. 4 shows the same cross sectional view as FIG. 3, after a first stage of introduction of the catheter according to FIG. 1 as far as the striated muscular sphincter;

FIG. 5 represents the following stage in which the means for temporary positioning of the catheter according to FIG. 1 is activated in the bulbar region of the urethra;

FIG. 6 represents the stage of positioning of the catheterization means according to FIG. 1, with the aid of the temporary positioning means;

FIG. 7 shows the final position of the catheterization means according to FIG. 1;

FIG. 8 represents the closure of the sphincter around the flexible connection means connecting the upper and lower tubular elements of the catheterization means according to FIG. 1;

FIG. 9 represents the catheter according to FIG. 1, after deactivation of the temporary positioning means, and separation of the introduction means from the catheterization means;

Figure 10:
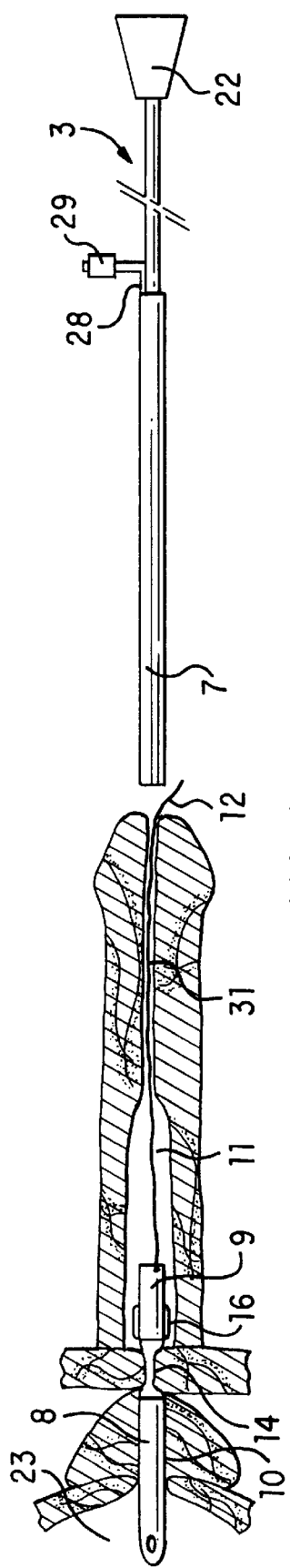
FIG. 10 represents the final position of the distal catheterization means according to FIG. 1, after complete removal of the proximal introduction means, showing the free passage for flow between the bladder and the bulbar urethra, under the control of the sphincter.

As is represented diagrammatically in FIGS. 1 and 2, a catheter according to the first embodiment of the invention is designated generally by the reference number 1. This catheter 1 comprises a distal means of catheterization 2 and a proximal means of introduction 3. As is shown in particular by the comparison between FIGS. 3 and 10, the distal means of catheterization 2 is at the outset joined to the introduction means 3 in an aligned or coaxial manner, for introduction of the catheter into the urethra, and finally, after the catheterization means 2 has been put into position, the introduction means 3 is disconnected and withdrawn from the urethra.

The catheterization means 2 is relatively flexible so as to adapt in shape to the natural dimensions and shape of the urethra in the prostatic region, but it is sufficiently rigid to maintain an artificial passage in this region. The means 2 includes at least one longitudinal lumen 5 passing through it from one end to the other, and it is intended and designed to be placed and held in the prostatic region.

The catheterization means 2 comprises two tubular elements, being an upper element 8 and a lower element 9, respectively, which are intended to be placed in the upper part 10 and the lower part 11 of the urethral channel, on either side of the striated muscular sphincter 13. The tubular elements 8 and 9 present the same inner cross section, with the same internal diameter. The upper and lower tubular elements 8 and 9 are connected to one another via a flexible and deformable connection means 14 which is intended to be placed in the orifice 13a of the sphincter 13. The connection means 14 permits the normal play of the striated muscular sphincter 13 and ensures the flow of the liquid between the upper and lower tubular elements 8, 9. This means consists of polyamide filaments, a tubular membrane or a tube of flexible material, for example polyethylene or polypropylene.

The upper tubular element 8 has, at its distal part, one or two drainage orifices 15 passing through its external wall and communicating with the longitudinal lumen 5. Its distal end is preferably flexible, for example synthetic foam, and its proximal end communicates with the connection means 14.

The lower tubular element 9 has, in addition to the lumen 5, an inflatable balloon 16 which circumscribes it and which is made of any suitable material, for example rubber, and is arranged at the distal end close to and below the connection means 14, for example 2 mm from the latter. The balloon 16, which is situated close to and below the connection means 14, has a preferred length of approximately 15 to 20 mm. The balloon can be fixed on or incorporated in the lower tubular element 9. FIG. 2 shows the shape of the balloon 16 in the deactivated state, that is to say deflated, while its activated state 16a, that is to say inflated, is represented by dot-dash lines. The balloon 16 is preferably made integral with the said tubular element 9 and can be inflated by way of a supplementary longitudinal connection passage 17 which is formed in the wall of this tubular element 9 and which communicates with a longitudinal lumen 27 of slightly greater diameter which is formed in the pusher tube 7 and with which the passage 17 is in alignment. The cross section of the connection passage 17 is smaller than that of the lumen 27 in the pusher tube 7. The connection passage 17 communicates with the balloon 16 via an orifice situated near the distal end of the lower tubular element 9. Advantageously, the lower tubular element 9 can also include a removal filament 12 which is secured in a proximal zone of the said element 9 and is intended to facilitate the removal of the catheterization means 2 if so required.

The introduction means 3 comprises, on the one hand, an outer pusher tube 7 of external diameter close to that of the two tubular elements 8, 9 of the catheterization means 2, and, on the other hand, a semirigid inner alignment rod 19 whose external cross section is adapted to the internal cross section of the tube 7 and of the catheterization means 2, that is to say of the two tubular elements 8 and 9, and whose length is adapted to intubate both the pusher tube 7 and the catheterization means 2. The pusher tube 7 thus has a length which is shorter than that of the alignment rod 19. The pusher tube 7 of the introduction means 3 has a main lumen 55 which communicates, in the same cross section, with the lumen 5 formed within the catheterization means. This tube 7 also includes communication means 18 for establishing a connection, on the one hand at its distal end 24, with the means 16 for temporary positioning of the lower tubular element 9, and, on the other hand at its opposite proximal end 25, with an external activation means 29, for activating the said temporary positioning means 16 using an external source of fluid. Preferably, as is represented in FIG. 2, the communication means 18 serve for the passage of the inflation fluid and are made up of the longitudinal lumen 27 and a hollow metal tube 28, for example a flexible cannula, for introduction of the inflation fluid. The hollow tube 28 has an external diameter which is greater than the internal diameter of the connection passage 17, so that the said tube 28 is inserted, in such a way as to be impervious to fluids, via its distal end into the proximal end of the connection passage 17. This hollow tube 28 has an external diameter which is smaller than that of the lumen 27, so as to permit its longitudinal displacement with functional clearance inside the said lumen.

The metal tube 28 is equipped with the activation or control means 29, controlling the flow of the inflation fluid, at its proximal end; and its distal end 32 provides for the communication with the balloon 16. The activation means 29, as represented in FIG. 2, constitutes a one-way cock, for example, or an injection valve, the axis of which is inclined in relation to the longitudinal axis of the tube. In the case where the metal tube 28 is a cannula or a needle, the latter passes through the entire length of the tube 7 and beyond its distal end 24, when the injection valve 29 is in abutment against the proximal end 25 of the tube 7. The means 30 for impervious connection with the balloon 16 thus consist, on the one hand, of the distal end 32 of the hollow metal tube 28, and, on the other hand, of the connection passage 17 provided in the lower tubular element 9 and connected in an impervious manner to the end 32.

The semirigid, hollow alignment rod 19 of the introduction means 3 has an external cross section which is adapted to be lodged in the lumina 5 and 55 of the catheterization means 2 and introduction means 3, a distal end 20 adapted to communicate with the inside of the upper tubular element 8, and an open proximal end 21 in the form of an abutment piece 22. This rod ensures the cohesion, unity and alignment of the catheterization means 2 and introduction means 3 prior to the insertion of the catheter, and it can slide along the lumina 5 and 55 with a suitable functional play. At its distal end, the rod is equipped with an eyelet or two eyelets (not shown) which communicate with the inside of the lumina 5 and 55 and are situated opposite the two orifices 15 of the upper tubular element 8, in the assembled position of the catheterization means 2 and introduction means 3. This allows the physician to confirm the entry of the catheter in the bladder 23, since there will then be a flow of urine.

Figure 11:
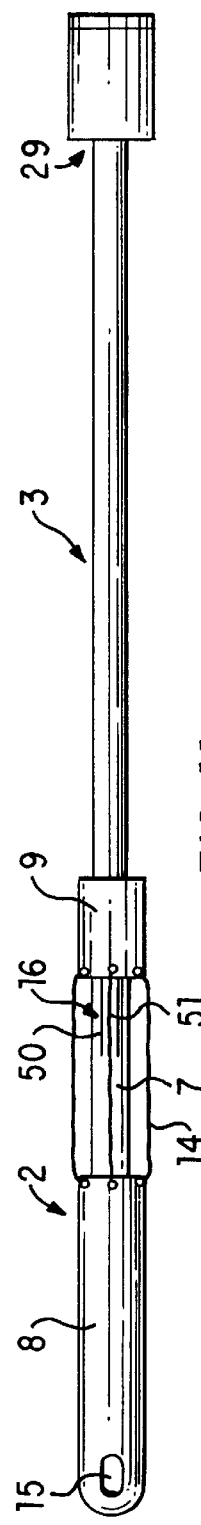
FIG. 11 represents a diagrammatic elevation of a separable catheter according to a second embodiment of the invention, in the retracted position of the bearing elements of the distal temporary positioning means.
Figure 12:
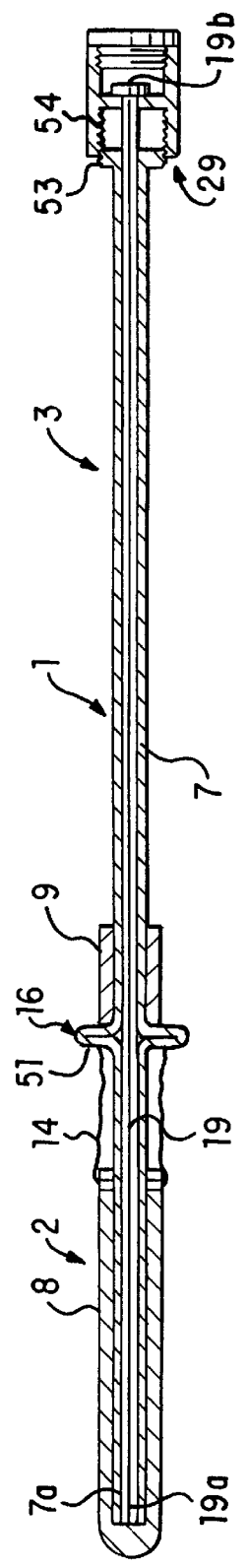
FIG. 12 represents the catheter according to FIG. 11, with a partial cross sectional view, in the deployed position of the bearing elements of the distal temporary positioning means.

The separable catheter represented in FIGS. 11 and 12, according to the second embodiment of the present invention, differs from that described above in terms of the following characteristics.

The introduction means 3 and more specifically the outer pusher tube 7 comprise the distal temporary positioning means 16.

The outer pusher tube 7 has an external diameter which is smaller than the internal diameter of the two tubular elements 8 and 9 of the catheterization means 2, in such a way as to permit a longitudinal displacement of the catheterization means 2, with functional clearance, on or in relation to the introduction means 3. Furthermore, the outer pusher tube 7 has a length which is substantially equal to that of the inner rod 19. The distal end 7a of the outer pusher tube 7 comes into abutment against the inner distal end of the upper tubular element 8 of the catheterization means 2. And the catheterization means 2 is arranged on the introduction means 3 in such a way that the distal temporary positioning means 16 is situated between the two tubular elements 8 and 9 of the catheterization means, that is to say prior to the positioning of the separable catheter. The inner rod 19 for its part has a length which is substantially equal to that of the outer pusher tube 7, and it is fixed in translation at its distal end 19a on the distal end 7a of the outer pusher tube 7.

The distal temporary positioning means 16 comprises a plurality of bearing elements 51 distributed about the outer pusher tube 7 and each designed to assume two positions, namely a radially retracted position, and a deployed position protruding radially from the outer pusher tube 7. To do this, the outer tube 7 includes locally, that is to say at the site of the distal temporary positioning means 16, axial cutouts 50 which form between them tongues 51. Each tongue 51 is radially foldable between two positions, namely a first position folded outward at its centre (cf. FIG. 12), and an unfolded position (cf. FIG. 11) in which it is included in the wall of the outer pusher tube 7. These tongues 51 thus form or constitute elements for bearing against the lower side of the striated muscular sphincter.

The external activation means 29 comprises a mechanical means for axially displacing the outer tube 7 in relation to the inner rod 19 and for correspondingly folding and unfolding the tongues 51 of the distal temporary positioning means 16. This mechanical means comprises a screw thread 53 arranged on the outside and at the distal end of the outer tube 7, and a collar 54 with internal screw thread cooperating with the screw thread 53, and bearing, free in terms of rotation, against the distal end 19b of the inner rod 19.

The positioning of the catheter according to the invention will now be described with reference to FIGS. 3 to 10 which are specific to the first embodiment, but which can be generalized to cover the second embodiment according to FIGS. 11 and 12.

FIG. 3 shows the assembled catheter, in the position ready for introduction, and a diagrammatic view of the male urethra. The latter comprises, in a general manner, five segments of very different diameter, length and orientation, namely:

a penile segment 31 of small diameter, approximately 100 mm long, and which is oriented in accordance with the position of the penis;

a bulbar segment 11 of large diameter, approximately 70 mm long, in a fixed and horizontal position;

a membranous segment 13a of small diameter, approximately 10 mm long, in a vertical position; it is the segment traversing the pelvic floor and the striated muscular sphincter 13;

and a prostatic segment 10 of variable diameter and geometry depending on the anatomy of the prostate, 30 to 70 mm long, and of vertical orientation.

These different orientations are not represented in the Figures, but it is important to remember that the bulbar urethra 11 has a much greater diameter than the other segments, and that the angle between the prostatic segment 10 and the bulbar segment 11 is of the order of 120°.

The catheter 1 is first introduced into the penile urethra 31 and then the bulbar urethra 11, until the physician senses its distal end making contact with the striated muscular sphincter 13 (cf. FIG. 4). The latter is permanently closed, apart from during micturition, and this means that a certain resistance has to be overcome in order to pass through it.

The activation of the temporary positioning means 16 is represented in FIG. 5. According to the first embodiment, the balloon 16 is inflated by the valve 29 with a suitable quantity of fluid, for example with 1.5 to 2 ml of sterile water. The wall of the balloon 16 comes to press flat against the wall of the bulbar segment 11 of the urethra whose diameter is, at this site, greater than that of the penile segment 31. According to the second embodiment, the tongues 51 are folded substantially at their centre and come up against the wall of the bulbar segment 11.

In the following stage (cf. FIG. 6), the physician advances the catheter until the means 16, within the bulbar segment 11, comes into abutment against the sphincter and is arrested by the latter. This allows the upper tubular element 8 to pass largely through the striated muscular sphincter 13.

The following stage, represented by FIG. 7, consists in tensioning the connection means 14, in this case polyamide filaments, by pushing the upper tubular element 8 with the introduction means 3, for example according to the first embodiment by pushing the element 8 with the inner rod 19 until its cone 22 comes into abutment against the proximal end 25 of the tube 7. This manoeuvre allows the said upper tubular element 8 to pass completely through the sphincter and to intubate the prostatic segment 10 in its entirety. The flow of urine through the inside of the inner rod 19 guarantees that the distal end of the upper tubular element 8 has entered the bladder.

FIG. 8 shows the beginning of the separation or disconnection of the catheterization means 2 and the introduction means 3. In particular, according to the first embodiment of the invention, the inner rod 19 is pulled back partially, by a length slightly greater than that of the catheterization means, once in place. At this moment, the striated muscular sphincter 13 closes around the connection means 14, thereby blocking the tubular elements 8 and 9 in the prostatic segment 10 and bulbar segment 11, respectively.

Then, according to the first embodiment of the invention, the needle 28 is pulled back by a length greater than that which intubated the supplementary passage 17 of the lower tubular element 9, for example by approximately 7 mm. The balloon then deflates immediately (cf. FIG. 9). According to the second embodiment of the invention, the tongues 51 are unfolded and merge substantially in the wall of the pusher tube 7.

FIG. 10 shows the final stage and the removal of the introduction means 3 en bloc. The physician in fact removes at one and the same time the inner rod 19, the pusher tube 7, and the needle 28 (according to the first embodiment).

The removal of the catheterization means 2 can be performed separately, by pulling on the proximal end of the lower tubular element 9, either with the aid of the filament 12, secured beforehand at this level, or with the aid of small forceps, under endoscopic monitoring.

We claim:

1. A detachable catheter apparatus for insertion into a bladder of a living being through a urethra of the living being to convey a fluid, comprising:

a tube assembly extending along a longitudinal axis and including a distal tube section having a closed end and an opposite opened end, a proximal tube section having a first end and an opposite second end and a connector fabricated from a flexible, deformable material, the connector connecting the opened end of the distal tube section and the first end of the proximal tube section together, the distal tube section including an orifice formed therethrough and sized to enable the fluid to enter the distal tube section so that the fluid can flow into and through the distal tube section, the connector and the proximal tube section;

an insertion device slidably receivable by the tube assembly, the insertion device including an elongated inner alignment rod having a contact end portion and an insertion end portion disposed opposite the contact end portion, the inner alignment rod sized to extend into the tube assembly wherein the contact end portion contacts the closed end of the distal tube section while the insertion end portion projects outwardly from the tube assembly;

an expandable member disposed circumferentially about and longitudinally along one of the proximal tube section and the insertion device adjacent the connector and operative to move between an expanded state wherein the expandable member expands radially outwardly and a collapsed state wherein the expandable member collapses; and an activation device operably connected to the expendable member and disposed externally of the urethra to cause the expandable member to move between the expanded state and the collapsed state.

2. A detachable catheter apparatus according to claim 1, wherein the expandable member is disposed circumferentially about and longitudinally along the proximal tube section.

3. A detachable catheter apparatus according to claim 2, wherein the expandable member is a balloon and is operative to move between the expanded state wherein the balloon expands radially outwardly and about the proximal tube section to form an expansion cavity and the collapsed state wherein the balloon radially embraces the proximal tube section with the expansion cavity collapsed around the proximal tube section.

4. A detachable catheter apparatus according to claim 3, wherein the insertion device includes an outer pusher tube having a bore extending longitudinally therethrough and sized to slidably receive the inner alignment rod, the outer pusher tube having a connecting end removably connected to the second end of the proximal tube section.

5. A detachable catheter apparatus according to claim 4, wherein the proximal tube section includes a conduit for fluid communication between the second end of the proximal tube section and the expansion cavity.

6. A detachable catheter apparatus according to claim 4, wherein the outer pusher tube includes a duct extending longitudinally therethrough.

7. A detachable catheter apparatus according to claim 6, further comprising an expansion tube having a first tube end portion and a second tube end portion disposed opposite the first tube end portion and sized to be slidably received by the duct and to project outwardly from the duct, wherein the expansion tube and the duct are oriented to align with the conduit in the proximal tube section so that the first tube end portion is slidably received by the conduit in a fluid-tight relationship.

8. A detachable catheter apparatus according to claim 7, further comprising a valve device connected to the second tube end of the expansion tube and operative between an opened condition wherein fluid communication is provided exteriorly of the detachable catheter apparatus with the expansion cavity and a closed condition wherein fluid communication is prevented exteriorly of the detachable catheter apparatus with the expansion cavity.

9. A detachable catheter apparatus according to claim 1, wherein the insertion device includes an outer pusher tube having a bore extending longitudinally therethrough and sized to slidably receive the inner alignment rod, the outer pusher tube having a connecting end removably connected to the second end of the proximal tube section.

10. A detachable catheter apparatus according to claim 9, wherein the expandable member is disposed longitudinally along the outer pusher tube, the expandable member is operative to move between the expanded state wherein the expandable member expands radially outwardly from the outer pusher tube and the collapsed state wherein the expandable member radially collapses to be an aligned portion of the outer pusher tube.

11. A detachable catheter apparatus according to claim 10, wherein the expandable member is a plurality of bearing elements.

12. A detachable catheter apparatus according to claim 1, wherein the insertion device includes an abutment piece connected to the insertion end portion of the inner alignment rod.

13. A detachable catheter apparatus according to claim 1, further comprising a tether fabricated from a flexible cord material and connected to the proximal tube section adjacent the second end.

14. A detachable catheter apparatus according to claim 1, wherein at least one of the tube assembly and the insertion device is fabricated from a stiff material.

* * * * *